US011273215B2

(12) United States Patent
Raychoudhuri

(10) Patent No.: US 11,273,215 B2
(45) Date of Patent: Mar. 15, 2022

(54) SYNTHETIC POLYPEPTIDE EPITOPE BASED VACCINE COMPOSITION

(71) Applicant: BHARAT BIOTECH INTERNATIONAL LIMITED, Hyderabad (IN)

(72) Inventor: Amit Raychoudhuri, Hyderabad (IN)

(73) Assignee: BHARAT BIOTECH INTERNATIONAL LIMITED, Hyderabad (IN)

( * ) Notice: Subject to any disclaimer, the term of this patent is extended or adjusted under 35 U.S.C. 154(b) by 323 days.

(21) Appl. No.: 16/628,057

(22) PCT Filed: Jul. 3, 2018

(86) PCT No.: PCT/IN2018/050433

§ 371 (c)(1),
(2) Date: Jan. 2, 2020

(87) PCT Pub. No.: WO2019/008599

PCT Pub. Date: Jan. 10, 2019

(65) Prior Publication Data

US 2021/0220466 A1 Jul. 22, 2021

(30) Foreign Application Priority Data

Jul. 3, 2017 (IN) ............................ 201741023411

(51) Int. Cl.

| | |
|---|---|
| ***A61K 39/135*** | (2006.01) |
| ***A61P 31/14*** | (2006.01) |
| ***C07K 1/22*** | (2006.01) |
| ***C07K 1/36*** | (2006.01) |
| ***C07K 14/09*** | (2006.01) |
| *A61K 39/00* | (2006.01) |

(52) U.S. Cl.
CPC ............ *A61K 39/135* (2013.01); *A61P 31/14* (2018.01); *C07K 1/22* (2013.01); *C07K 1/36* (2013.01); *C07K 14/09* (2013.01); *A61K 2039/70* (2013.01)

(58) Field of Classification Search
None
See application file for complete search history.

(56) References Cited

U.S. PATENT DOCUMENTS 9,109,014 B2 8/2015 Weiner et al.

FOREIGN PATENT DOCUMENTS

WO 2016073929 5/2016

OTHER PUBLICATIONS

International Search Report and Written Opinion issued in PCT/IN2018/050433 dated Oct. 15, 2018.

*Primary Examiner* — Stacy B Chen
(74) *Attorney, Agent, or Firm* — Bakerhostetler

(57) ABSTRACT

Conserved epitopes selected from EV71 and CVA16, the two major causative agents of Hand Foot and Mouth Disease has been used to develop sub-unit bivalent vaccine antigen construct. The said vaccine described in this invention is capable to provide cross-protection to diverse EV71 and CVA16 infection causing strains. Further disclosed are the expression of the multi-epitope vaccine antigen coding gene and the purification process involved thereof. This present invention also discloses vaccine formulations against Hand Foot and Mouth Disease and other enterovirus infections comprising the recombinant vaccine antigen construct of the present invention.

17 Claims, 10 Drawing Sheets
(6 of 10 Drawing Sheet(s) Filed in Color)

Specification includes a Sequence Listing.

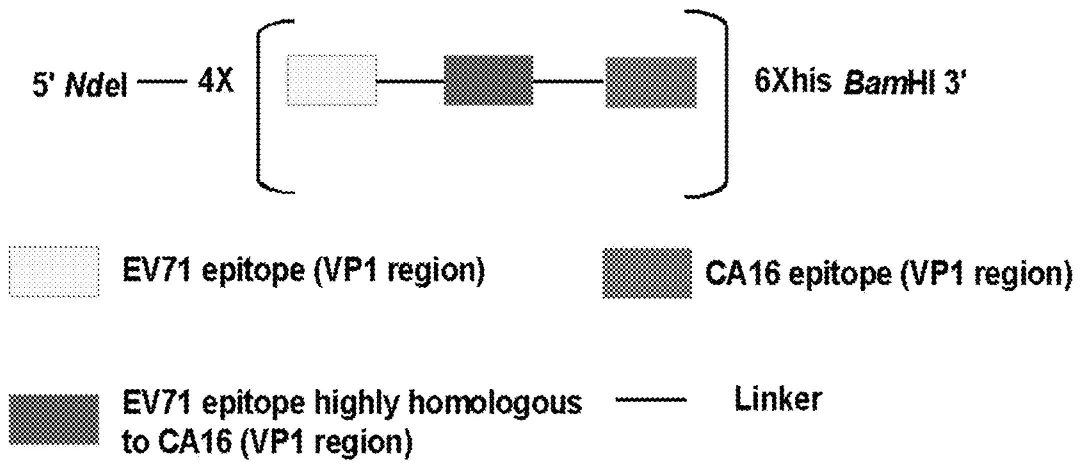
(1A)
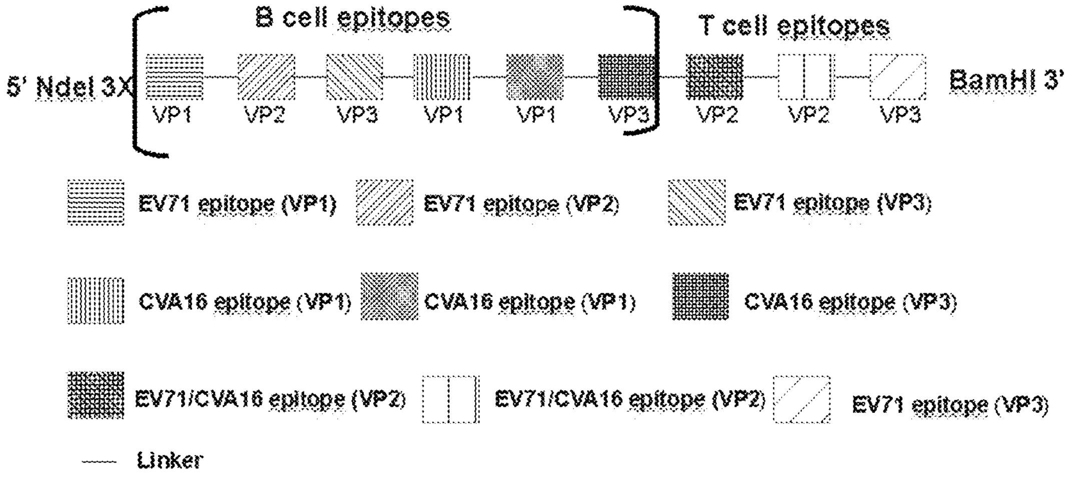
(1B)
Figure: 1
5' NdeI —— 4X [ ▢ ▬ ▬ ] 6Xhis BamHI 3'
▢ EV71 epitope (VP1 region)    ▬ CA16 epitope (VP1 region)
▬ EV71 epitope highly homologous to CA16 (VP1 region)    —— Linker
(1A)
5' NdeI 3X [ B cell epitopes | T cell epitopes ] BamHI 3'
VP1 VP2 VP3 VP1 VP1 VP3 | VP2 VP2 VP3
▬ EV71 epitope (VP1)   ▨ EV71 epitope (VP2)   ▨ EV71 epitope (VP3)
▬ CVA16 epitope (VP1)   ▨ CVA16 epitope (VP1)   ▬ CVA16 epitope (VP3)
▬ EV71/CVA16 epitope (VP2)   ▢ EV71/CVA16 epitope (VP2)   ▨ EV71 epitope (VP3)
—— Linker
(1B)

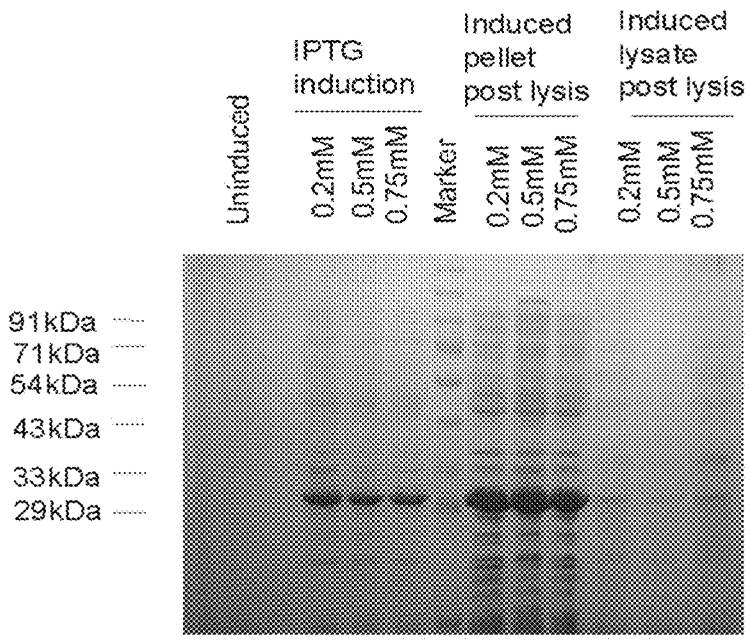
(2A)
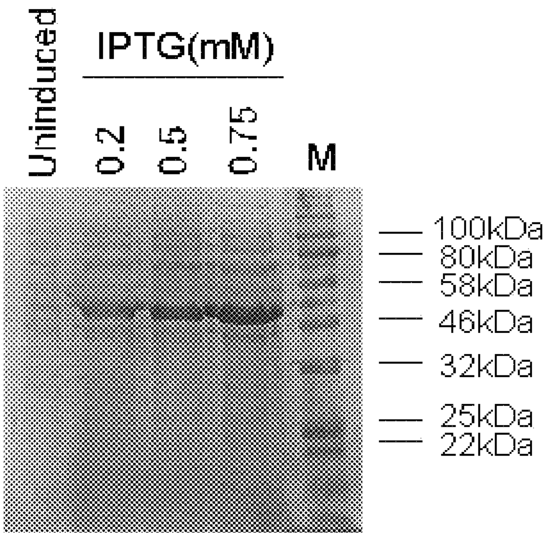
(2B)
Figure: 2

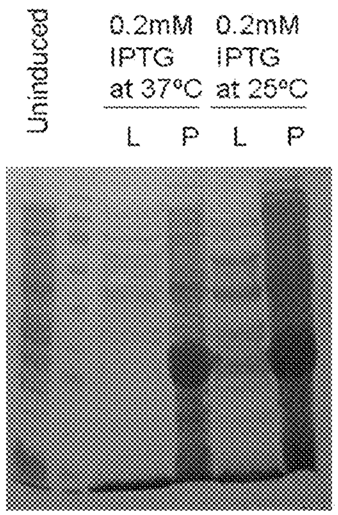
(3A)
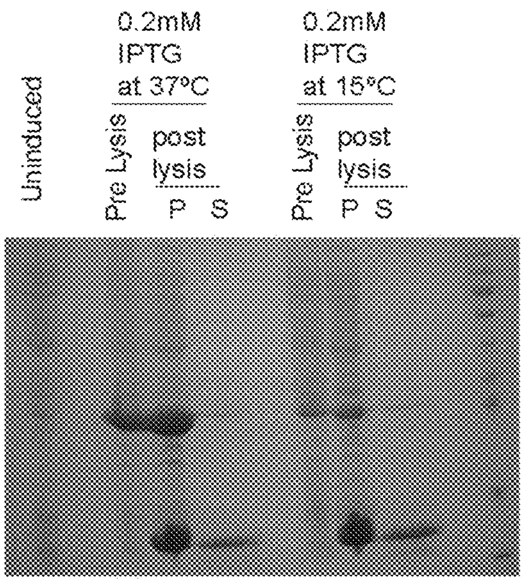
(3B)
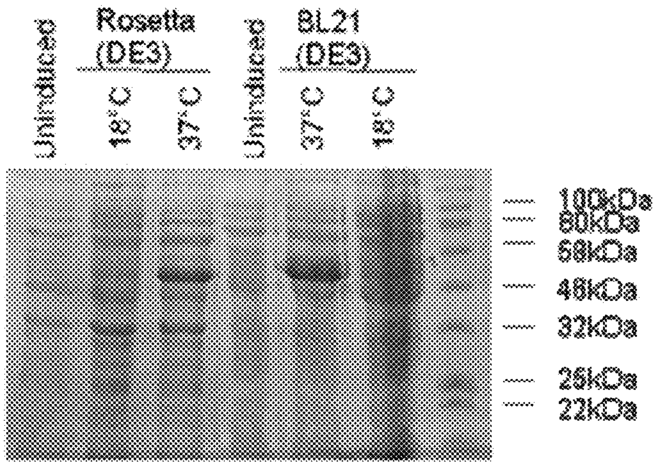
(3C)
Figure: 3

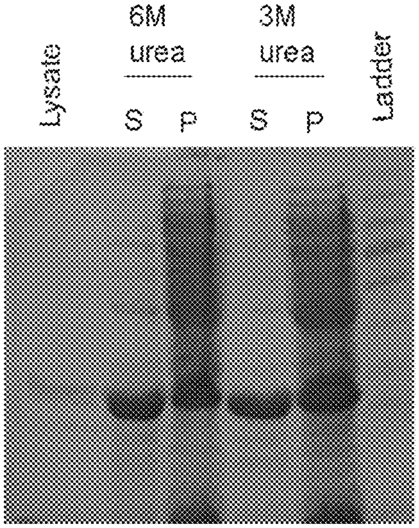
(4A)
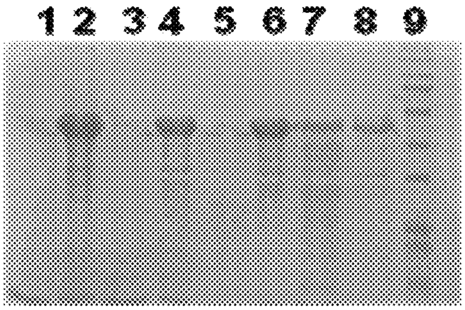
(4B)
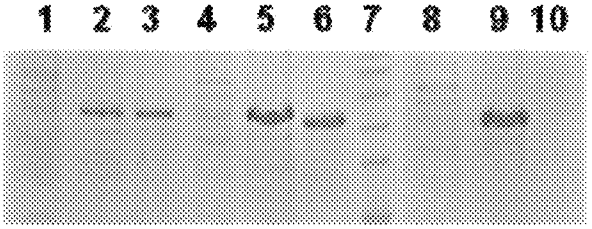
(4C)
Figure: 4

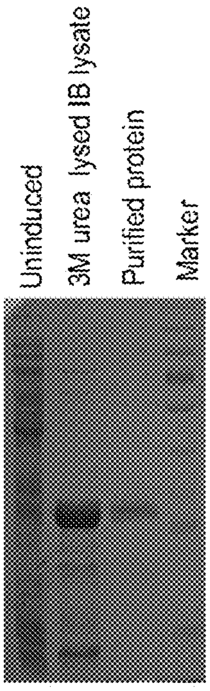
(5A)
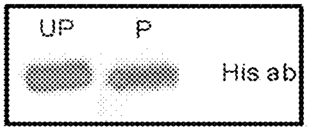
(5B)
Figure: 5

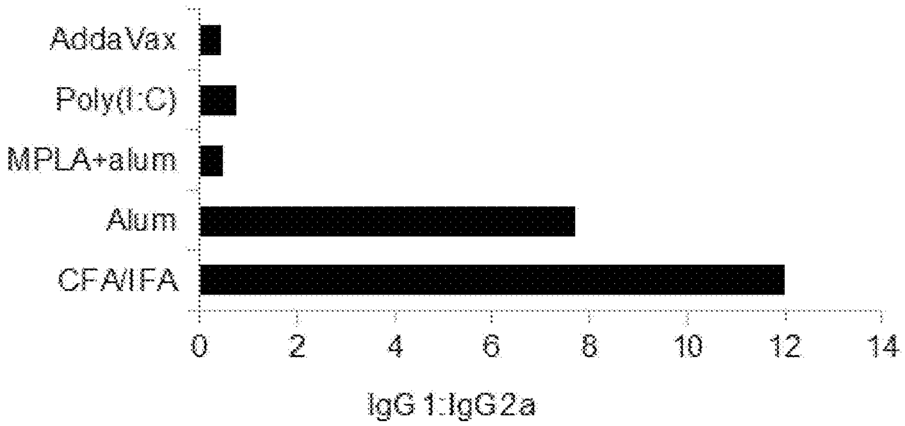
Figure: 6

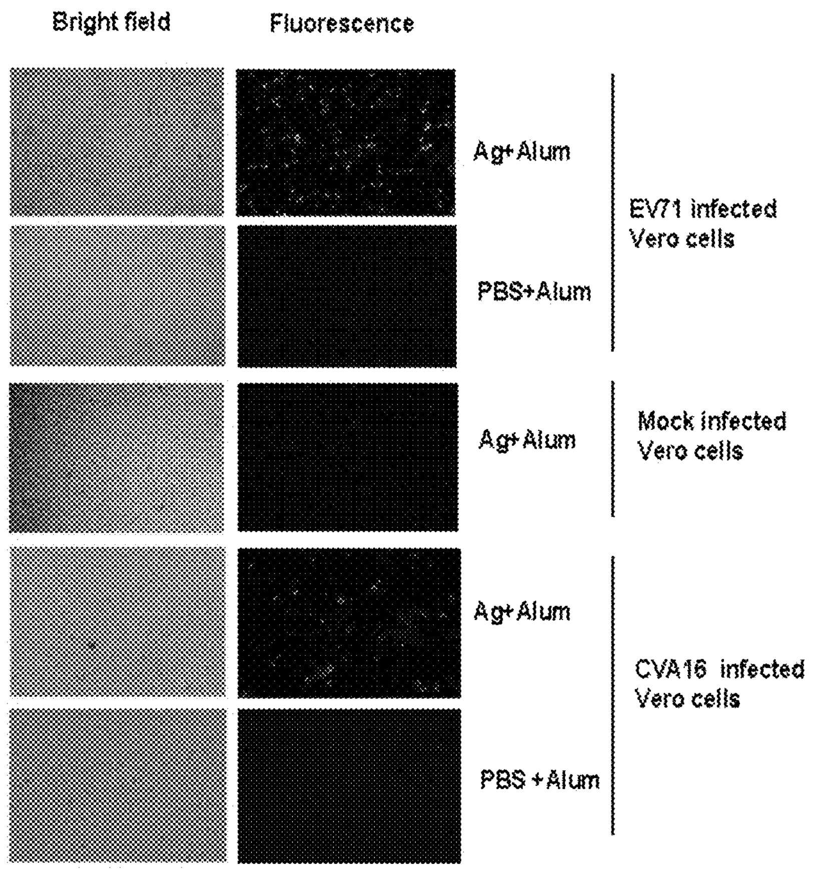
Figure: 7

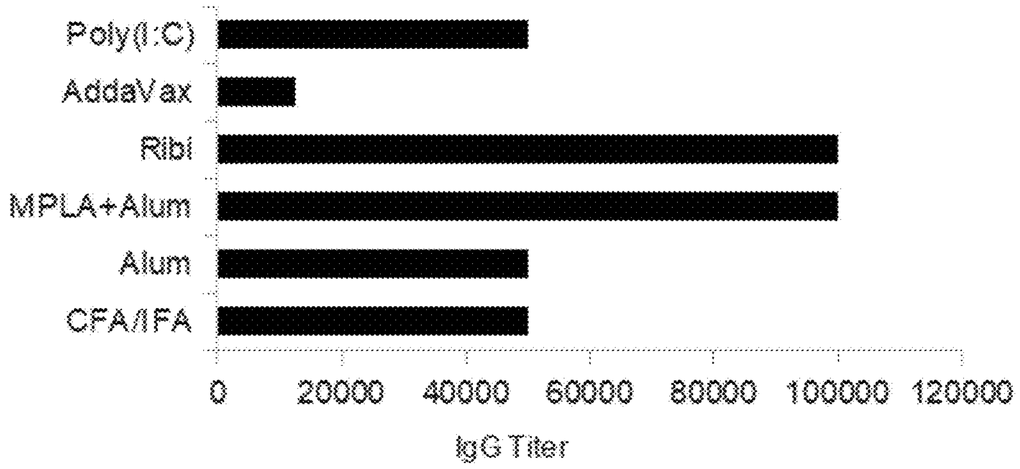
Figure: 8

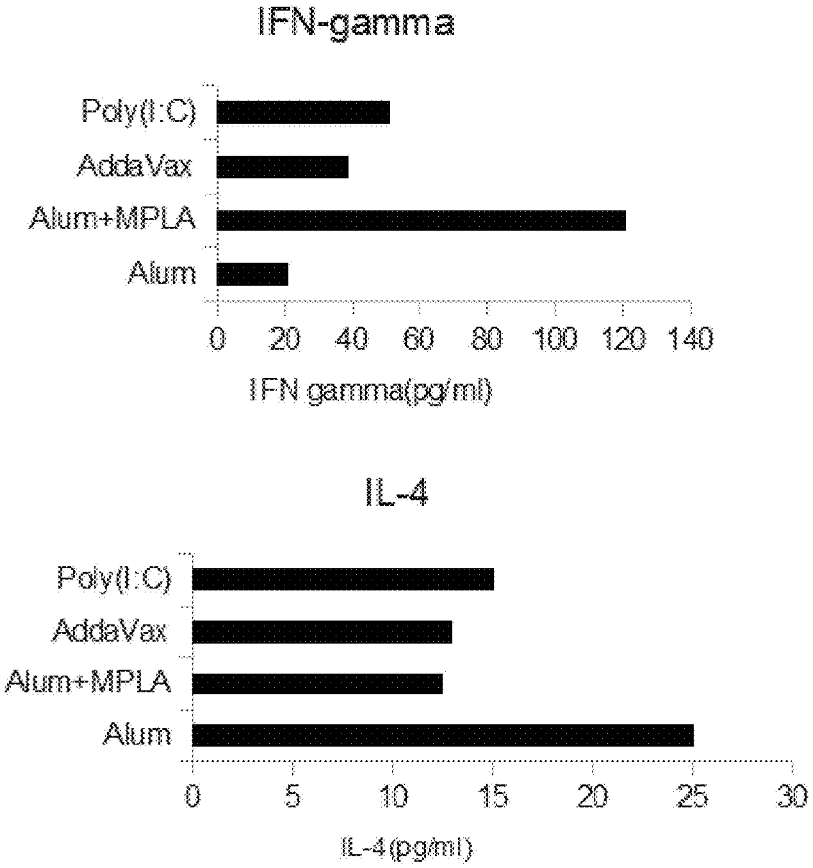
Figure: 9

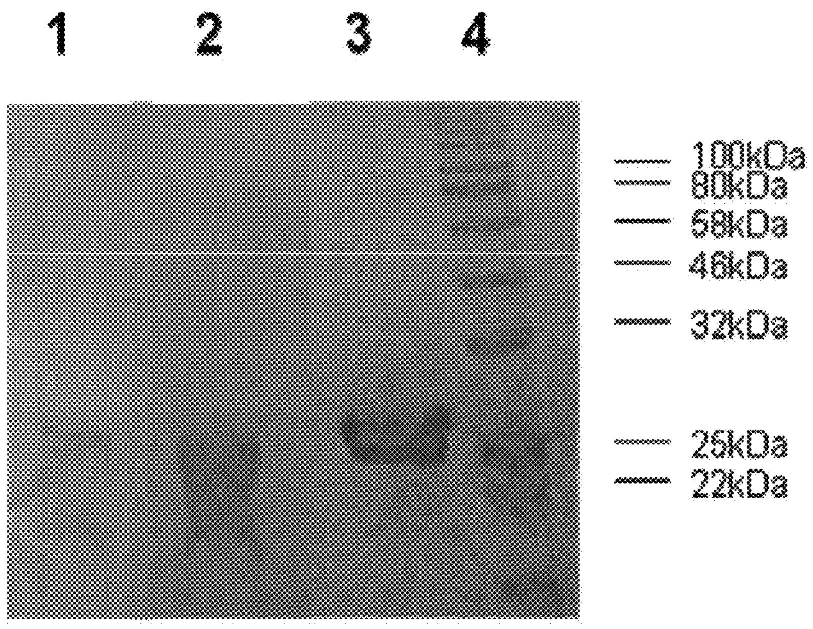
Figure: 10

SEQUENCE LISTING

```
<160> NUMBER OF SEQ ID NOS: 4

<210> SEQ ID NO 1
<211> LENGTH: 777
<212> TYPE: DNA
<213> ORGANISM: Artificial Sequence
<220> FEATURE:
<223> OTHER INFORMATION: Nucleic acid sequence of Multi-epitope
      Enterovirus antigen 1 (MEV1)

<400> SEQUENCE: 1

catatggctg caggttctgg ttacgacggt tacccgacct tcggtgaaca caaacaggaa     60

aaagacctgg aatacggtgg ttctggtggt tacctgttca aaaccaaccc gaactacaaa    120

ggtaacgaca tcaaaggtgg ttctggtggt atgcgtatga aacacgttcg tgcttggata    180

ccgcgtatgc gtggtggttc tggtggttac gacggttacc cgaccttcgg tgaacacaaa    240

caggaaaaag acctggaata cggtggttct ggtggttacc tgttcaaaac caacccgaac    300

tacaaaggta acgacatcaa aggtggttct ggtggtatgc gtatgaaaca cgttcgtgct    360

tggataccgc gtatgcgtgg tggttctggt ggttacgacg gttacccgac cttcggtgaa    420

cacaaacagg aaaaagacct ggaatacggt ggttctggtg gttacctgtt caaaaccaac    480

ccgaactaca aaggtaacga catcaaaggt ggttctggtg gtatgcgtat gaaacacgtt    540

cgtgcttgga taccgcgtat gcgtggtggt tctggtggtt acgacggtta cccgaccttc    600

ggtgaacaca aacaggaaaa agacctggaa tacggtggtt ctggtggtta cctgttcaaa    660

accaacccga actacaaagg taacgacatc aaaggtggtt ctggtggtat gcgtatgaaa    720

cacgttcgtg cttggatacc gcgtatgcgt catcatcacc atcaccacta aggatcc       777


<210> SEQ ID NO 2
<211> LENGTH: 255
<212> TYPE: PRT
<213> ORGANISM: Artificial Sequence
<220> FEATURE:
<223> OTHER INFORMATION: Amino acid sequence of Multi-epitope
      Enterovirus antigen 1 (MEV1)

<400> SEQUENCE: 2

Met Ala Ala Gly Ser Gly Tyr Asp Gly Tyr Pro Thr Phe Gly Glu His
1               5                   10                  15

Lys Gln Glu Lys Asp Leu Glu Tyr Gly Gly Ser Gly Gly Tyr Leu Phe
            20                  25                  30

Lys Thr Asn Pro Asn Tyr Lys Gly Asn Asp Ile Lys Gly Gly Ser Gly
        35                  40                  45
```

-continued

```
Gly Met Arg Met Lys His Val Arg Ala Trp Ile Pro Arg Met Arg Gly
    50                  55                  60

Gly Ser Gly Gly Tyr Asp Gly Tyr Pro Thr Phe Gly Glu His Lys Gln
65                  70                  75                  80

Glu Lys Asp Leu Glu Tyr Gly Gly Ser Gly Gly Tyr Leu Phe Lys Thr
                85                  90                  95

Asn Pro Asn Tyr Lys Gly Asn Asp Ile Lys Gly Gly Ser Gly Gly Met
            100                 105                 110

Arg Met Lys His Val Arg Ala Trp Ile Pro Arg Met Arg Gly Gly Ser
        115                 120                 125

Gly Gly Tyr Asp Gly Tyr Pro Thr Phe Gly Glu His Lys Gln Glu Lys
    130                 135                 140

Asp Leu Glu Tyr Gly Gly Ser Gly Gly Tyr Leu Phe Lys Thr Asn Pro
145                 150                 155                 160

Asn Tyr Lys Gly Asn Asp Ile Lys Gly Gly Ser Gly Gly Met Arg Met
                165                 170                 175

Lys His Val Arg Ala Trp Ile Pro Arg Met Arg Gly Gly Ser Gly Gly
            180                 185                 190

Tyr Asp Gly Tyr Pro Thr Phe Gly Glu His Lys Gln Glu Lys Asp Leu
        195                 200                 205

Glu Tyr Gly Gly Ser Gly Gly Tyr Leu Phe Lys Thr Asn Pro Asn Tyr
    210                 215                 220

Lys Gly Asn Asp Ile Lys Gly Gly Ser Gly Gly Met Arg Met Lys His
225                 230                 235                 240

Val Arg Ala Trp Ile Pro Arg Met Arg His His His His His His
                245                 250                 255


<210> SEQ ID NO 3
<211> LENGTH: 1359
<212> TYPE: DNA
<213> ORGANISM: Artificial Sequence
<220> FEATURE:
<223> OTHER INFORMATION: Nucleic acid sequence of Multi-epitope
      Enterovirus antigen 2 (MEV2)

<400> SEQUENCE: 3

catatgcgtc gtggcagcta tgatggttat ccgaccttcg gcgagcacaa acaagaaaaa      60

gacctggaat acggcggcgg cagcgcgggc ggcaccggca ccgaggacag ccacccgccg     120

tataaacaaa cccaaccggg tgcgggtggc ggtagcgtga acaacgttcc gaccaacgcg     180

accagcctga tggagcgtct gggcggtccg ggctacccga ccttcggtga acacctgcaa     240

gcgaacgacc tggattatgg ccagtgcggc ggtggcagca accaaccgta cctgtttaaa     300

accaacccga actataaggg taacgacatc aaaggtggcg gtagccacta ccgtgcgcac     360

gcgcgtgcgg gttatttcga ctactatacc ggtccgggtc cgtacgatgg ctatccgacc     420

tttggcgagc acaagcagga aaaagacctg gagtatggcg gtggcagcgc gggtggcacc     480

ggcaccgaag atagccaccc gccgtacaaa caaacccagc cgggtgcggg tggcggtggc     540

agcgtgaata atgtgccgac caatgcgacc agcctgatgg aacgtctggg tggcccgggc     600

tatccgacct ttggcgaaca cctgcaagcg aatgacctgg attacggcca atgcggcggt     660

ggcagcaatc agccgtacct gtttaagacc aatccgaatt ataagggcaa cgacattaaa     720

ggtggcagcc actatcgtgc gcacgcgcgt gcggggtact ttgactacta taccggtccg     780

ggtccgtacg atggctatcc gacgtttggt gaacacaagc aggagaaaga cctggaatat     840

ggtggtggta gcgcgggtgg caccggcacc gaggatagcc acccgccgta taaacaaacg     900
```

```
caaccgggtg cgggcggtgg cagcgtgaat aatgttccta ctaatgctac cagcctgatg     960

gaacgcctgg gtggtccggg ttacccgact tttggcgaac acctgcaagc aaatgacctg    1020

gattatggcc aatgcggtgg cggtagcaat caaccttacc tgtttaagac taacccgaac    1080

tataagggca acgacatcaa aggcggtggc agccactatc gtgcgcacgc gcgtgcgggc    1140

tatttcgatt actataccgc gggcgcgggt gcgcagctga ccatcggtaa cagcaccatt    1200

accacccaag aagcggcgaa catcggcggt ggcagcccgc accagtggat taacctgcgt    1260

accaacaact gcgcgaccat cattggtggc ggtagcatgg cgaccggtaa aatgctgatt    1320

gcgtacaccc cgccgggtgg tccgctgccg taaggatcc                           1359


<210> SEQ ID NO 4
<211> LENGTH: 449
<212> TYPE: PRT
<213> ORGANISM: Artificial Sequence
<220> FEATURE:
<223> OTHER INFORMATION: Amino acid sequence of Multi-epitope
      Enterovirus antigen 2 (MEV2)

<400> SEQUENCE: 4

Met Arg Arg Gly Ser Tyr Asp Gly Tyr Pro Thr Phe Gly Glu His Lys
1               5                   10                  15

Gln Glu Lys Asp Leu Glu Tyr Gly Gly Gly Ser Ala Gly Gly Thr Gly
            20                  25                  30

Thr Glu Asp Ser His Pro Pro Tyr Lys Gln Thr Gln Pro Gly Ala Gly
        35                  40                  45

Gly Gly Ser Val Asn Asn Val Pro Thr Asn Ala Thr Ser Leu Met Glu
    50                  55                  60

Arg Leu Gly Gly Pro Gly Tyr Pro Thr Phe Gly Glu His Leu Gln Ala
65                  70                  75                  80

Asn Asp Leu Asp Tyr Gly Gln Cys Gly Gly Gly Ser Asn Gln Pro Tyr
                85                  90                  95

Leu Phe Lys Thr Asn Pro Asn Tyr Lys Gly Asn Asp Ile Lys Gly Gly
            100                 105                 110

Gly Ser His Tyr Arg Ala His Ala Arg Ala Gly Tyr Phe Asp Tyr Tyr
        115                 120                 125

Thr Gly Pro Gly Pro Tyr Asp Gly Tyr Pro Thr Phe Gly Glu His Lys
    130                 135                 140

Gln Glu Lys Asp Leu Glu Tyr Gly Gly Gly Ser Ala Gly Gly Thr Gly
145                 150                 155                 160

Thr Glu Asp Ser His Pro Pro Tyr Lys Gln Thr Gln Pro Gly Ala Gly
                165                 170                 175

Gly Gly Gly Ser Val Asn Asn Val Pro Thr Asn Ala Thr Ser Leu Met
            180                 185                 190

Glu Arg Leu Gly Gly Pro Gly Tyr Pro Thr Phe Gly Glu His Leu Gln
        195                 200                 205

Ala Asn Asp Leu Asp Tyr Gly Gln Cys Gly Gly Gly Ser Asn Gln Pro
    210                 215                 220

Tyr Leu Phe Lys Thr Asn Pro Asn Tyr Lys Gly Asn Asp Ile Lys Gly
225                 230                 235                 240

Gly Ser His Tyr Arg Ala His Ala Arg Ala Gly Tyr Phe Asp Tyr Tyr
                245                 250                 255

Thr Gly Pro Gly Pro Tyr Asp Gly Tyr Pro Thr Phe Gly Glu His Lys
            260                 265                 270
```

-continued

```
Gln Glu Lys Asp Leu Glu Tyr Gly Gly Gly Ser Ala Gly Gly Thr Gly
        275                 280                 285

Thr Glu Asp Ser His Pro Pro Tyr Lys Gln Thr Gln Pro Gly Ala Gly
    290                 295                 300

Gly Gly Ser Val Asn Asn Val Pro Thr Asn Ala Thr Ser Leu Met Glu
305                 310                 315                 320

Arg Leu Gly Gly Pro Gly Tyr Pro Thr Phe Gly Glu His Leu Gln Ala
                325                 330                 335

Asn Asp Leu Asp Tyr Gly Gln Cys Gly Gly Gly Ser Asn Gln Pro Tyr
            340                 345                 350

Leu Phe Lys Thr Asn Pro Asn Tyr Lys Gly Asn Asp Ile Lys Gly Gly
        355                 360                 365

Gly Ser His Tyr Arg Ala His Ala Arg Ala Gly Tyr Phe Asp Tyr Tyr
    370                 375                 380

Thr Ala Gly Ala Gly Ala Gln Leu Thr Ile Gly Asn Ser Thr Ile Thr
385                 390                 395                 400

Thr Gln Glu Ala Ala Asn Ile Gly Gly Gly Ser Pro His Gln Trp Ile
                405                 410                 415

Asn Leu Arg Thr Asn Asn Cys Ala Thr Ile Ile Gly Gly Gly Ser Met
            420                 425                 430

Ala Thr Gly Lys Met Leu Ile Ala Tyr Thr Pro Pro Gly Gly Pro Leu
        435                 440                 445

Pro
```

SYNTHETIC POLYPEPTIDE EPITOPE BASED VACCINE COMPOSITION

CROSS-REFERENCE TO RELATED APPLICATIONS

This application is a 371 of International Patent Application No. PCT/IN2018/050433 filed Jul. 3, 2018, which claims priority to Indian Patent Application No. 201741023411, filed Jul. 3, 2017. These applications are incorporated herein by reference in their entireties for any and all purposes.

SEQUENCE LISTING

The instant application contains a Sequence Listing which has been submitted electronically in ASCII format and is hereby incorporated by reference in its entirety. Said ASCII copy, created on Apr. 5, 2021, is named 10833.021520 Substitute Sequence Listing.txt and is 9,494 bytes in size.

FIELD OF THE INVENTION

The invention relates to a synthetic polypeptide epitope based vaccine composition. More particularly, conserved epitopes selected from EV71 and CVA16 are used to develop a sub-unit bivalent vaccine antigen construct and a vaccine composition is provided using the developed sub-unit bivalent vaccine antigen construct, wherein the vaccine is capable to provide cross protection to diverse EV71 and CVA16 infection causing strains. Further the expression of multi-epitope vaccine antigen coding gene and the purification process involved thereof are disclosed. The invention also discloses vaccine formulations against Hand Foot and Mouth Disease and other enterovirus infections comprising the recombinant vaccine antigen construct of the present invention.

BACKGROUND OF THE INVENTION

Hand foot and mouth disease (HFMD) is a common pediatric disease caused predominantly by Enterovirus-71 (EV71) and coxsackievirus A16 (CVA16). Both of them are single stranded positive-sense RNA viruses and belong to Picornaviridae family. EV71 also causes numerous neurological complications ranging from aseptic meningitis to acute flaccid paralysis, brain-stem encephalitis and even death. Often these two viruses co-circulate and cause co-infection bringing devastating impact on healthcare system of many Asian countries.

EV71 and CVA16 are the two major etiological agents against Hand Foot and mouth Disease. Both of the viruses are highly polymorphic and antibody(ies) against one will not provide significant cross-protection against the other. Thus, a probable bivalent protein composition against these two viruses immense promise to reduce the global burden of this disease. It is well known that majority of the neutralizing antibody is located in major capsid protein VP1 among enteroviruses. VP1 has lot of sequence variability among different strains due to frequent mutations and recombination events (Leitch E C M et al. J. Virol. 2012; 86:2676-2685). Based on the VP1 sequence variation, EV71 has been classified so far into seven genogroups (GgA-GgG) and genogroups B and C are further subdivided into B1-B5 and C1-C5 (Brown B A et al. J. Virol. 1999; 73:9969-9975).

Thus, development of vaccine against both of these viruses is highly desirable to constrain them. The inventors of this present invention proposes and hereby has developed a vaccine directed mainly against EV71 and CA16 with potentiality to cross protect against other closely circulating HFMD causing serogroups. An unique synthetic gene encoding multiple copies of epitopes derived from capsid protein (VP1) from Enterovirus-71 and Coxsackievirus-A16 have been designed and constructed to be used as a distinct and highly effective recombinant protein construct with potential for immunization as a vaccine candidate against hand foot and mouth infections caused by EV71 and CA16.

Further, the inventors have also developed and disclosed in this invention another vaccine candidate that encompass epitopes regions from the major capsid proteins VP1, VP2 and VP3 of EV71 and CVA16.

Objective of the Invention

In one object, the invention provides a synthetic polypeptide epitope based vaccine composition.

In another object, the invention provides a recombinant sub-unit bivalent vaccine antigen construct using conserved epitopes selected from EV71 and CVA16.

In another object, the invention provides a vaccine which is capable to provide cross-protection to diverse EV71 and CVA16 infection causing strains.

In another object, the invention further provides the expression of the multi-epitope vaccine antigen coding gene and the purification process involved thereof.

In another object, the invention provides vaccine formulations against Hand Foot and Mouth Disease and other enterovirus infections comprising the recombinant vaccine antigen construct of the present invention.

SUMMARY OF THE INVENTION

According to one embodiment of the invention, the schematic structure and the codon optimized genetic and protein sequences of multi-epitope based vaccine antigens against hand foot and mouth disease is disclosed.

According to another embodiment of the invention, the expression of codon optimized sequences of the present invention as inclusion bodies in appropriate host is disclosed.

Further embodiment of the invention describes the method of protein purification comprising lysis with lysis buffer-I and lysis buffer-II, washing with wash buffers I, II, and III, Immobilized metal affinity chromatography followed by dialysis and refolding and recovery of the proteins of interest of SEQ ID No. 2 and SEQ ID No. 4 with appropriate refolding buffers, subsequently followed by specific chromatographic purification techniques such as size exclusion chromatography.

The further embodiments of the invention also establish immunogenicity of the invention through appropriate animal studies. The SEQ ID Nos. 2 and 4 is capable to generate sufficient immune response against Hand Foot and Mouth disease caused by enterovirus and coxsackievirus. The vaccine antigens of the present invention are also capable to induce cross-protection against any strains of enterovirus and coxackievirus causing hand foot and mouth disease in humans.

Specific vaccine formulations comprising SEQ ID No. 2 and SEQ ID No. 4 with multiple adjuvants have also been made available as one of the embodiments of the present invention optionally in presence of other stabilizers like polyols, sugar or amino acids or combinations.

In another aspect of the instant invention there is provided a vaccine composition for prophylaxis against Hand Foot and Mouth Disease caused by EV71 and CA16 comprising: (a) vaccine antigen, the said vaccine antigen is a synthetic construct selected from the recombinant protein sequences as represented by SEQ ID No. 2 (named as MEV1) and SEQ ID No. 4 (named as MEV2); (b) adjuvants; (c) stabilizers; and (d) any physiologically acceptable buffer selected from phosphate, and citrate, wherein the said vaccine formulation is stable for at least 2 years at 5±3° C. and up to 2 weeks at 37° C.

BRIEF DESCRIPTION OF THE FIGURES

The file of this patent or application contains at least one drawing/photograph executed in color. Copies of this patent or patent application publication with color drawings will be provided by the Office upon request and payment of the necessary fee.

FIG. 1: Multi-epitope bivalent vaccine gene construct against Enterovirus A71 and Coxsackievirus A16 (MEV1 and MEV2).

1A: The schematic representation of MEV1 showed that four copies of the three epitopes are present in tandem. Linker separates the epitopes to add flexibility. NdeI and BamHI sequences are present at the 5' and 3' end respectively.

1B: The schematic representation of MEV2 showed that three copies of six epitopes are present in tandem followed by one copy of three more epitopes. Linker separates the epitopes to add flexibility. NdeI and BamHI sequences are present at the 5' and 3' end respectively.

FIG. 2: Different concentration of IPTG has been evaluated to assess the optimum concentration for expression of MEV1 (2A) and MEV2 (2B). 2A: From left Lane 1: Un-induced cells (in absence of IPTG), Lane2-4: Cells induced with 0.2 mM, 0.5 mM and 0.75 mM IPTG respectively, Lane 5: Molecular weight marker for protein with sizes 16 kDa, 29 kDa, 33 kDa, 43 kDa, 54 kDa, 71 kDa, 91 kDa, 124 kDa and 250 kDa respectively from bottom, Lane 6-8: Cell pellet with protein aggregates after induced with 0.2 mM, 0.5 mM and 0.75 mM IPTG respectively and followed by lysis, Lane 9-11: Cell lysate after induced with 0.2 mM, 0.5 mM and 0.75 mM IPTG respectively and followed by lysis.

2B: From Left, Lane1: Un-induced BL21 (DE3) cells transformed with pET11b-MEV2 (in absence of IPTG), Lane 2-4: Induction of BL21 (DE3) cells transformed with pET11b-MEV2 using 0.2 mM, 0.5 mM and 0.75 mM IPTG Conclusion: The results from the figure showed that expression of MEV1 and MEV2 can be induced using wide range of IPTG concentration.

FIG. 3: The level of expression of MEV1 (3A, 3B) and MEV2 (3C) is evaluated in different temperature settings.

(3A):—From left Lane 1: Un-induced cells (in absence of IPTG), Lane 2: Molecular weight protein marker as described in FIG. 1, Lane 3-4: Cell lysate and cell pellet respectively after induced with 0.2 mM IPTG at 37° C. and followed by lysis, Lane 4-5: Cell lysate and cell pellet respectively after induced with 0.2 mM IPTG at 25° C. and followed by lysis.

(3B):—From left Lane 1: Un-induced cells (in absence of IPTG, Lane 2: Cells induced with IPTG at 37° C., Lane 3-4: Cell pellet (P) and cell lysate (S) respectively after induced with 0.2 mM IPTG at 37° C. and followed by lysis, Lane 5: Cells induced with IPTG at 25° C., Lanes 6-7: Cell pellet (P) and cell lysates (S) respectively after induced with 0.2 mM IPTG at 25° C. and followed by lysis, Lane 8: Molecular weight protein marker as described in FIG. 1.

(3C): From left Lane1: Un-induced MEV2 gene transformed Rosetta cells (in absence of IPTG), Lane 2: Rosetta cells induced with 0.2 mM IPTG at 18° C., Lane 3: Rosetta cells induced with 0.2 mM IPTG at 37° C., Lane4: Un-induced MEV2 gene transformed BL21 (DE3) cells, Lane 5: BL21 (DE3) cells induced with 0.2 mM IPTG at 37° C., Lane 6: BL21 (DE3) cells induced with 0.2 mM IPTG at 18° C., Lane 7: Molecular weight protein marker.

Conclusion: The results obtained from FIGS. 3A and 3B depicted that 37° C. is the optimum temperature to induce MEV1 and MEV2 by IPTG.

FIG. 4: Two different concentrations of urea (6M and 3M) were evaluated for improving the solubility of MEV1 (4A) while for MEV2, solubility was also assessed with two different concentrations of urea (6M and 3M) in presence or absence of DTT with variable pH (4B, 4C).

4A: From left Lane 1: Cell lysate after induced with 0.2 mM IPTG and followed by lysis, Lane 2: Supernatant after insoluble cell aggregates was treated with 6M urea, Lane 3: Cell pellet after insoluble cell aggregates was treated with 6M urea, Lane 4: Supernatant after insoluble cell aggregates was treated with 3M urea, Lane 5: Cell pellet after insoluble cell aggregates was treated with 3M urea, Lane 6: Molecular weight protein marker as described in FIG. 1.

4B: From left, Lane1: Supernatant after insoluble cell aggregates was treated with 3M urea, Lane 2: Cell pellet after insoluble cell aggregates was treated with 3M urea, Lane 3: Supernatant after insoluble cell aggregates was treated with 3M urea in presence of 10 mM DTT, Lane 4: Cell pellet after insoluble cell aggregates was treated with 3M urea in presence of 10 mM DTT, Lane 5: Supernatant after insoluble cell aggregates was treated with 6M urea, Lane 6: Cell pellet after insoluble cell aggregates was treated with 6M urea, Lane 7: Supernatant after insoluble cell aggregates was treated with 6M urea in presence of 10 mM DTT, Lane 8: Cell pellet after insoluble cell aggregates was treated with 6M urea in presence of 10 mM DTT, Lane 9: Molecular weight protein marker as described in FIG. 2B.

4C: From Lane 1: Cell lysate after induced with 0.2 mM IPTG and followed by lysis in Lysis buffer I (ph7.4), Lane 2: supernatant after insoluble cell aggregates was treated with 6M urea in lysis buffer II (ph7.4) in presence of 20 mM DTT, Lane 3: cell pellet after insoluble cell aggregates was treated with 6M urea in Lysis buffer II (ph7.4) in presence of 20 mM DTT, Lane 4: Cell lysate after induced with 0.2 mM IPTG and followed by lysis in lysis buffer (50 mM $Na_2HPO_4$, 0.3M NaCl, 1% TritonX-114, 0.5 mg/ml lysozyme, 1 mM AEBSF, at pH 8), Lane 5: supernatant after insoluble cell aggregates was treated with 6M urea in lysis buffer 50 mM $Na_2HPO_4$, 0.3M NaCl, 1% TritonX-114, 0.5 mg/ml lysozyme, 1 mM AEBSF, at pH 8) in presence of 20 mM DTT, Lane 6: Cell pellet after insoluble cell aggregates was treated with 6M urea in lysis buffer 50 mM $Na_2HPO_4$, 0.3M NaCl, 1% TritonX-114, 0.5 mg/ml lysozyme, 1 mM AEBSF, at pH 8) in presence of 20 mM DTT, Lane 7: Molecular weight protein marker as described in FIG. 2B, Lane 8: Cell lysate after induced with 0.2 mM IPTG and followed by lysis in lysis buffer (50 mM Tris; 0.3 M NaCl, 1% TritonX-114, 0.5 mg/ml lysozyme, 1 mM AEBSF, at pH 8.5), Lane 9: supernatant after insoluble cell aggregates was treated with 6M urea in lysis buffer (50 mM Tris, 0.3M NaCl, 1% TritonX-114, 0.5 mg/ml lysozyme, 1 mM AEBSF, at pH 8.5) in presence of 20 mM DTT, Lane 10: Cell pellet after insoluble cell aggregates was treated with 6M urea in lysis buffer (50 mM Tris, 0.3M NaCl, 1% TritonX-114, 0.5 mg/ml lysozyme, 1 mM AEBSF, at pH 8.5) in presence of 20 mM DTT (The volume of cell pellet was very less for Lane 10 sample as it got solubilized well).

Conclusion: The figure concludes that the 3M and 6M urea treatment can be recovered with significant amounts of MEV1 with higher purity when compared to the untreated samples whereas presence of 6M urea and DTT is required to achieve significant amount of soluble MEV2 protein.

FIG. 5: Expression and purification of EV-Ag (MEV1). (5A): Expressed MEV1 was purified by affinity chromatography with IMAC technology using Ni-NTA resins and SDS-PAGE electrophoresis was performed). From left Lane 1: Un-induced cell pellet (in absence of IPTG), Lane 2: Supernatant from inclusion bodies (IB) like cell aggregates treated with 3M urea, Lane 3: Purified protein after IMAC mediated purification using N-NTA resin, Lane 4: Molecular weight protein marker as described in FIG. 1.

(5B): The specific expression of MEV1 was detected by Western Blot using anti-his antibody. From left Lane 1: (UP)—Unpurified protein in supernatant derived from inclusion bodies (IB) like cell aggregates after treatment with 3M urea, Lane 2: (P)—Purified protein after IMAC mediated purification using Ni-NTA resin.

Conclusion: The results from FIG. 5 showed that the IMAC purification step generated more than 90% purified MEV1 and the specific expression was confirmed by western blotting using anti-his antibody.

FIG. 6: IgG1/IgG2a ratio was determined for the MEV1 immunized Balb/C mice sera (1:250) in presence of different adjuvants. CFA/IFA: Mice immunized with MEV1 in presence of Complete Freud's adjuvant as prime dose and MEV1 in presence of Incomplete Freud's adjuvant as subsequent booster dose, Alum: Mice immunized with MEV1 in presence of Alum as adjuvant, MPLA+ Alum: Mice immunized with MEV formulated with Alum and MPLA both. Poly(I:C): Mice immunized with MEV formulated with Poly(I:C), AddaVax: Mice immunized with MEV formulated with AddaVax. MEV1 coated ELISA plates were treated with the sera (1:250) and finally incubated with either anti-mouse IgG1-HRP or IgG2a-HRP secondary antibody.

Conclusion: CFA/IF And Alum adjuvanted MEV1 immunization generated much higher IgG1 antibody indicating predominant Th2 type immune response while Poly(I:C), AddaVax and MPLA+ Alum generated slightly higher IgG2a antibody indicating overall balanced Th1/Th2 response with slight bias for Th1 type immune response.

FIG. 7: Binding analysis of MEV1 immunized sera with EV71 and CVA16 by Immunofluorescence. Sera were collected from mice immunized with MEV1 formulated with Alum or from mice immunized with PBS formulated with alum. Subsequently, Vero cells were infected with either Enterovirus A71 (EV71) and Coxsackievirus A16 (CVA16) at 0.01 Multiplicity of Infection. Infected Vero cells were treated with 1:200 diluted sera as mentioned in the corresponding panel of the figure followed by incubation with Alexa 488 conjugated anti-mouse IgG secondary antibody and observed under fluorescence microscope. Bright field: Bright field of the microscope, Fluorescence: Green fluorescent field of the microscope, Ag+ Alum: Sera collected from mice immunized with MEV1 formulated with Alum, PBS+ Alum: Sera collected from mice immunized with PBS formulated with Alum (negative control sera), EV71 infected Vero cells: Panels where Vero cells infected with EV71 has been used, CVA16 infected Vero cells: Panels where Vero cells infected with CVA16 has been used, Mock infected Vero cells: Panels where Vero cells were not infected with virus (negative control for infected Vero cells).

Conclusion: Immunofluorescence result showed the cross-reactivity of the antibody generated against both EV71 and CVA16.

FIG. 8: IgG Titer of the serum from MEV-1 antigen immunized mice in presence of different Adjuvants. Serum was collected two-weeks after the $2^{nd}$ boost. ELISA was performed in the antigen coated ELISA plate in presence of different concentration of serum following blocking. Subsequently, Secondary IgG-HRP conjugated antibody was added. TMB substrate was added for colour generation which was stopped with 0.6-1M HCL. The color intensity was recorded at 450 nm in an ELISA reader.

FIG. 9: Quantitation of IFN-γ (9A) and IL-4 (9B) secreted from splenocytes of mice immunized with MEV1 formulated with different adjuvants.

FIG. 10: Stability of the synthetic protein construct MEV-1, from Left, Lane 1: MEV1 protein without stabilizer at 37±12° C. for 2 weeks, Lane 2: MEV1 protein in 20% Glycerol at 37±12° C. for 2 weeks, Lane 3: MEV1 protein not exposed to 37±12° C. (control protein), Lane 4: Molecular weight protein marker.

DETAILED DESCRIPTION OF THE INVENTION

In the present invention, four copies of each epitope was connected by linkers to construct the recombinant antigen Multi-epitope Enterovirus antigen 1 (MEV1) that functions as a vaccine antigen gene construct. The target gene (MEV1) as disclosed in SEQ ID No.1 and the resultant protein as disclosed in SEQ ID No. 2 is designed to possess four copies of each of one enterovirus A71 epitope, one coxsackievirus A16 epitope and one extremely conserved epitope having 100% homology to enterovirus A71 strains and high homology to Coxsackievirus A16 and some other Coxsackievirus strains and thus will provide cross protection. All the epitopes are present in VP1 capsid gene of either Enterovirus A71 or Coxsackievirus A16. The target gene with NdeI and BamH1 restriction sites at 5' and 3' end respectively was used as insert to be introduced in NdeI-BamHI cloning site of the expression vector pET11b. The insert also include C-terminal 6× histidine for easy detection and purification of the expressed protein. The presence of poly-histidine tag enables the protein to be purified by immobilized metal affinity chromatography in the subsequent steps and also aids in the detection of the expression using poly-histidine specific antibody. 6× histidine tag has several advantages including smaller size, low toxicity and immunogenicity and thus doesn't interfere with the immunogenicity of the antigen. The vector with the insert was transformed in the *E. coli* DH5α (specifically for cloning) and BL21 (DE3) cells for expression of the said gene construct of the present invention.

The present invention also includes another construct MEV2 that includes nine epitopes from VP1-3 proteins of EV71 CVA16 (MEV2). These epitopes includes both B cell and T cell epitopes. The target gene (MEV2) sequence is disclosed in SEQ ID no 3 and the resultant protein sequence is disclosed in SEQ ID no 4.

```
SEQ ID No 1: Nucleic acid sequence of MEV1
CATATGGCTGCAGGTTCTGGTTACGACGGTTACCCGACCTTCGGTGAACA

CAAACAGGAAAAAGACCTGGAATACGGTGGTTCTGGTGGTTACCTGTTCA
```

-continued

AAACCAACCCGAACTACAAAGGTAACGACATCAAAGGTGGTTCTGGTGGT

ATGCGTATGAAACACGTTCGTGCTTGGATACCGCGTATGCGTGGTGGTTC

TGGTGGTTACGACGGTTACCCGACCTTCGGTGAACACAAACAGGAAAAAG

ACCTGGAATACGGTGGTTCTGGTGGTTACCTGTTCAAAACCAACCCGAAC

TACAAAGGTAACGACATCAAAGGTGGTTCTGGTGGTATGCGTATGAAACA

CGTTCGTGCTTGGATACCGCGTATGCGTGGTGGTTCTGGTGGTTACGACG

GTTACCCGACCTTCGGTGAACACAAACAGGAAAAAGACCTGGAATACGGT

GGTTCTGGTGGTTACCTGTTCAAAACCAACCCGAACTACAAAGGTAACGA

CATCAAAGGTGGTTCTGGTGGTATGCGTATGAAACACGTTCGTGCTTGGA

TACCGCGTATGCGTGGTGGTTCTGGTGGTTACGACGGTTACCCGACCTTC

GGTGAACACAAACAGGAAAAAGACCTGGAATACGGTGGTTCTGGTGGTTA

CCTGTTCAAAACCAACCCGAACTACAAAGGTAACGACATCAAAGGTGGTT

CTGGTGGTATGCGTATGAAACACGTTCGTGCTTGGATACCGCGTATGCGT

CATCATCACCATCACCACTAAGGATCC (The location of Ndel and BamH1 sites has been underlined and the location of the 6X histidine has been shown in bold in the actual sequences in SEQ ID No. 1 above)

SEQ ID No 2: Amino acid sequence of MEV1
MAAGSGYDGYPTFGEHKQEKDLEYGGSGGYLFKTNPNYKGNDIKGGSGGM

RMKHVRAWIPRMRGGSGGYDGYPTFGEHKQEKDLEYGGSGGYLFKTNPNY

KGNDIKGGSGGMRMKHVRAWIPRMRGGSGGYDGYPTFGEHKQEKDLEYGG

SGGYLFKINPNYKGNDIKGGSGGMRMKHVRAWIPRMRGGSGGYDGYPTFG

EHKQEKDLEYGGSGGYLFKTNPNYKGNDIKGGSGGMRMKHVRAWIPRMRH

HHHHH

SEQ ID No 3: Nucleic acid sequence of MEV2
CATATGCGTCGTGGCAGCTATGATGGTTATCCGACCTTCGGCGAGCACAA

ACAAGAAAAAGACCTGGAATACGGCGGCGGCAGCGCGGGCGGCACCGGCA

CCGAGGACAGCCACCCGCCGTATAAACAAACCCAACCGGGTGCGGGTGGC

GGTAGCGTGAACAACGTTCCGACCAACGCGACCAGCCTGATGGAGCGTCT

GGGCGGTCCGGGCTACCCGACCTTCGGTGAACACCTGCAAGCGAACGACC

TGGATTATGGCCAGTGCGGCGGTGGCAGCAACCAACCGTACCTGTTTAAA

ACCAACCCGAACTATAAGGGTAACGACATCAAAGGTGGCGGTAGCCACTA

CCGTGCGCACGCGCGTGCGGGTTATTTCGACTACTATACCGGTCCGGGTC

CGTACGATGGCTATCCGACCTTTGGCGAGCACAAGCAGGAAAAAGACCTG

GAGTATGGCGGTGGCAGCGCGGGTGGCACCGGCACCGAAGATAGCCACCC

GCCGTACAAACAAACCCAGCCGGGTGCGGGTGGCGGTGGCAGCGTGAATA

ATGTGCCGACCAATGCGACCAGCCTGATGGAACGTCTGGGTGGCCCGGGC

TATCCGACCTTTGGCGAACACCTGCAAGCGAATGACCTGGATTACGGCCA

ATGCGGCGGTGGCAGCAATCAGCCGTACCTGTTTAAGACCAATCCGAATT

ATAAGGGCAACGACATTAAAGGTGGCAGCCACTATCGTGCGCACGCGCGT

GCGGGGTACTTTGACTACTATACCGGTCCGGGTCCGTACGATGGCTATCC

GACGTTTGGTGAACACAAGCAGGAGAAAGACCTGGAATATGGTGGTGGTA

GCGCGGGTGGCACCGGCACCGAGGATAGCCACCCGCCGTATAAACAAACG

CAACCGGGTGCGGGCGGTGGCAGCGTGAATAATGTTCCTACTAATGCTAC

CAGCCTGATGGAACGCCTGGGTGGTCCGGGTTACCCGACTTTTGGCGAAC

ACCTGCAAGCAAATGACCTGGATTATGGCCAATGCGGTGGCGGTAGCAAT

CAACCTTACCTGTTTAAGACTAACCCGAACTATAAGGGCAACGACATCAA

AGGCGGTGGCAGCCACTATCGTGCGCACGCGCGTGCGGGCTATTTCGATT

ACTATACCGCGGGCGCGGGTGCGCAGCTGACCATCGGTAACAGCACCATT

ACCACCCAAGAAGCGGCGAACATCGGCGGTGGCAGCCCGCACCAGTGGAT

TAACCTGCGTACCAACAACTGCGCGACCATCATTGGTGGCGGTAGCATGG

CGACCGGTAAAATGCTGATTGCGTACACCCCGCCGGGTGGTCCGCTGCCG

TAAGGATCC

SEQ ID No 4: Amino acid sequence of MEV2
MRRGSYDGYPTFGEHKQEKDLEYGGGSAGGTGTEDSHPPYKQTQPGAGGG

SVNNVPTNATSLMERLGGPGYPTFGEHLQANDLDYGQCGGGSNQPYLFKT

NPNYKGNDIKGGGSHYRAHARAGYFDYYTGPGPYDGYPTFGEHKQEKDLE

YGGGSAGGTGTEDSHPPYKQTQPGAGGGGSVNNVPTNATSLMERLGGPGY

PTFGEHLQANDLDYGQCGGGSNQPYLFKTNPNYKGNDIKGGSHYRAHARA

GYFDYYTGPGPYDGYPTFGEHKQEKDLEYGGGSAGGTGTEDSHPPYKQTQ

PGAGGGSVNNVPTNATSLMERLGGPGYPTFGEHLQANDLDYGQCGGGSNQ

PYLFKTNPNYKGNDIKGGGSHYRAHARAGYFDYYTAGAGAQLTIGNSTIT

TQEAANIGGGSPHQWINLRTNNCATIIGGGSMATGKMLIAYTPPGGPLP

Furthermore, the recombinant genetic constructs of the present invention of the said vaccine antigen disclosed in this invention may comprise B cell or T cell epitopes from any enterovirus including but not limiting to EV71, EVD68, Coxsackievirus A16, Coxsackievirus A4-6, Coxsackievirus A10, echoviruses etc. The multi-epitope construct(s) mentioned in this invention may also include carrier protein(s) for better immunogenicity that may include any toxoids, TLR ligands like flagellin either as whole protein or truncated protein, CTL epitopes, T helper epitopes, immunomodulants, virus like particles etc. The antigen gene may also include one or more tags like poly-histidine tags, V5 tag, GST tag, signal sequences etc.

The proposed recombinant genetic constructs of the present invention can be expressed in bacteria, yeast, mammalian cell or virus. The vector may be plasmid or viral vector. In one embodiment, the expression system is *Escherichia coli*. Codon optimization is an essential step for successful production of heterologous protein in *E. coli*. In the present invention, MEV1 and MEV2 gene have been codon optimized for successful production in *E. coli*. In *E. coli* expression system, the heterologous protein often forms insoluble aggregates and remains inside the cells as inclusion bodies even after lysis with bacterial lysis buffer. Inclusion Body (IB) Proteins. All inclusion body proteins are highly specific in their bio-chemical properties, Each inclusion body forming protein needs specific experimental combinations such as specific combination of wash buffers for washing and cell lysis, denaturation components of the protein followed by refolding in specific refolding buffers of the said target protein for appropriate functional protein structure. Downstream processing including cell lysis, denaturation and refolding of any inclusion body forming protein generated from a synthetic recombinant genetic construct is far more difficult and unpredictable since the natural properties of the said protein are not at all known initially as compared to those proteins already available in nature but produced as inclusion body forming proteins through human intervention.

In the present invention, phosphate buffer has been used for MEV1 as it is non-toxic and a common component of physiological fluids. Its pH alters little with temperature. It is colourless and thus doesn't interfere with light absorbance during protein quantitation. Further, NaCl is used to reduce the nonspecific hydrophobic protein interactions. Lysozyme was used as it enhances cell lysis by acting on bacterial cell wall peptidoglycan. In the present invention, freeze thaw cycles and sonication has been used for disruption of bacterial cell leading to complete lysis. Short pulse of sonication has been used with chilling in ice in between to avoid high temperature generation that will degrade the protein. 4-(2-Aminoethyl) benzenesulfonyl fluoride (AEBSF) is a broad spectrum serine protease inhibitor and is non-toxic. AEBSF has been used in this invention to prevent the serine protease mediated degradation of MEV1. 4-(2-Aminoethyl)benzenesulfonyl fluoride hydrochloride or AEBSF is a serine-protease inhibitor that prevent serine proteases mediated degradation of protein. In another embodiment either phosphate buffer (ph7.4-8) or Tris buffer (ph8-8.5) have been used for lysis and solubilization of MEV1 and MEV2. Tris lysis buffer consists of 20-50 mM Tris, 0.3M NaCl, 1% TritonX-114, 0.5 mg/ml lysozyme, 1 mM AEBSF, at ph8-8.5.

TritonX-114 is a mild non-ionic detergent. It is used in cell lysis. It also has role in endotoxin reduction by phase separation at temperature higher than 20° C. Imidazole is a competitor for histidine to bind IMAC resins. Thus, in low concentration, it prevents non-specific binding and thus added in wash buffers. In higher concentration (varies between different proteins), it will release the tagged proteins and the desired protein will come in the elutes. The function of these specific components have been strategically optimized at each specific step that would best suit the present invention for these new proteins from the novel genetic construct of the present invention MEV1, MEV2 or similar constructs comprising enterovirus epitopes. These components are included as part of purification procedure in this present invention.

In general, the denaturating agents like urea or Guanidine HCl are used to denature any IB protein. In this process, the protein will get denatured and will come out in the solution. But, later protein can be renatured and refolded by stepwise or gradient decrease of urea concentration. However often, some specific additional components are required those technically assist in refolding and/or thereby prevent the aggregation of the varied category of IB proteins depending upon there bonding and three dimensional structures. L-Arginine and L-Arginine HCl has been found to be essential in preventing the aggregation of MEV1 and MEV2 of this present invention. Reducing agents like DTT or DTE is suitable for solubilizing MEV2.

The purification steps may involve affinity purification, size exclusion chromatography, ion exchange chromatography or any of the combinations thereof. The buffer(s) used for washing and purification of the recombinant protein derived from the recombinant genetic construct in this present invention includes phosphate buffer, Tris buffer, MOPS buffer etc.

The recombinant protein(s) in this invention can be formulated with adjuvants that includes but not limited to alum (aluminium phosphate, aluminium hydroxide), squalene based adjuvants like MF59, montanide etc, RIBI adjuvants, Complete Freud's adjuvant and Incomplete freud's adjuvant for immunogenicity testing, adjuvant involving bacterial cell components or modified versions such as MPL, muramyl dipeptide etc, all oil-in-water emulsions, all water-in-oil emulsions, TLR ligand based adjuvants, CpG and non CpG containing oligonucleotides, saponins including but not limited to QS-1, ISCOM, ISCOMATRIX etc, vitamins, immunomodulants including cytokines.

The route of administration of the vaccine can be oral or parenteral where parenteral route includes but not limiting to intramuscular, intranasal, subcutaneous, tropical, intradermal or transdermal.

Example 1: Expression of the Recombinant Protein of the Present Invention from MEV1 and MEV2 Genetic Construct The plasmid pET11b and pET11b-MEV1 was transformed in *E. coli* BL21 (DE3) chemically competent cells. The transformed BL21 (DE3) cells were incubated with shaking at 37° C. until $OD_{600}$ reaches 0.4 to 0.6, and then induced with different concentration of Isopropyl β-D-1-thiogalactopyranoside (IPTG) at 37° C. for 4 hours. IPTG is a molecular mimic of a lactose metabolite that triggers the transcription of lac operon and thus induces the expression of the recombinant protein where the gene is controlled by the lac operator. The optimum concentration of IPTG for expression was determined and then the induction of the multi-epitope gene (MEV1) for expression was also determined at various temperature settings (FIG. 3). The optimum condition for expression was assessed for future batches of experiments. pET11b-MEV2 was also transformed in BL21 (DE3) cells followed by incubation with shaking at 37° C. until $OD_{600}$ reaches 0.4 to 0.6, and then induced with different concentration of Isopropyl β-D-1-thiogalactopyranoside (IPTG) at 37° C. for 4 hours. The optimum condition for expression was also determined.

Example 2: Cell Lysis with Lysis Buffer-I and Lysis Buffer-II

The cell pellet of MEV1 transformed BL21 (DE3) after IPTG induction was collected by centrifuging the cells at 10,000 rpm for 5 mins. The cells were suspended in suspension/lysis buffer-I, the said lysis buffer-I was prepared by making a solution containing 50 mM $Na_2HPO_4$, 0.3M NaCl, 1% TritonX-114, 0.5 mg/ml lysozyme, 1 mM AEBSF, at pH 7.4. Cell lysis was performed first by performing three rounds of freeze thaw cycles and subsequently by ultrasonicating for 20 seconds thrice with 30 sec interval in between. The location of the desired protein was again checked by SDS-PAGE. The majority of the desired protein was found in cell debris indicating formation of insoluble inclusion/inclusion like bodies. The cells were then lysed in Lysis Buffer-II with different concentrations of urea (3-6M) in presence of 5-10 mM imidazole, 50 mM $Na_2HPO_4$, 0.3M NaCl, and 1 mM AEBSF at 4° C. for 3-16 hours to recover the insoluble protein.

Results showed that the recombinant enterovirus vaccine gene (MEV1) was induced best using 0.2 mM IPTG at 37° C. The protein was found to be expressed ~31 kDa region (FIG. 2) which coincide with the theoretical molecular weight of the protein calculated. To detect the extent of lysis, The SDS-PAGE analysis of the lysed cell free supernatant showed that only ~10% of the protein was present in the supernatant and the rest in the cell pellet (FIG. 2). The level of expression of the desired gene has not improved significantly at 25° C. (FIG. 3A) and at 15° C. (FIG. 3B) in comparison to that at 37° C. Thus, 37° C. has been selected as optimum temperature for expression of MEV1. Then, the cells were treated with 3M and 6M urea denaturation buffer to increase the recombinant protein recovery. It was found that up to ~65% of the protein can be recovered with ~2-5% difference in protein recovery using two different urea concentrations along with the increase of purity (FIG. 4 and Table 1). For the ease of renaturation, 3M urea concentration was selected to be used for later batches.

MEV-2 was also found to be expressed well in presence of 0.2-0.75 mM IPTG at ~47 kDa region (FIG. 2B). MEV2 didn't express well at 15-18° C. The expression was only found at ~37° C. MEV-2 expressed well when transformed in both BL21 (DE3) and Rosetta cells. Like MEV1, MEV2 didn't lyse well in presence of Lysis Buffer-I (FIG. 4C). Lysis Buffer-I for MEV2 comprised 50 mM Tris, 0.3 M NaCl, 1% Triton X114, 0.5 mg/ml lysozyme, 1 mM AEBSF at pH 8-8.5. Unlike MEV-1, MEV-2 didn't lyse and solubilize properly in presence of 3M urea. The solubility was slightly better in 6M urea. As, MEV2 protein sequence have four cysteine molecules, we predicted the presence of disulphide bonds in MEV2 native protein. Therefore, the addition of reducing agents like DTT can aid in disrupting the disulphide bond/s and thus will increase the solubility. We found that MEV2 protein get lysed and solubilized in lysis buffer-II that comprised 50 mM Tris, 0.3 M NaCl, 1 mM AEBSF in presence of 6M urea and 10-20 mM DTT. No significant solubility has been observed in presence of 3M urea and DTT at pH of 8-8.5.

Example 3: Immobilized Metal Affinity Chromatography (IMAC) and Washing of MEV 1 with Wash Buffer-I, II and Wash Buffer-III The urea denatured protein solution in presence of 5-10 mM imidazole was added to the Ni-NTA IMAC columns after equilibrating with lysis buffer-II and incubated for proper binding at 4° C. for 3-16 hrs. The column was then washed with Wash Buffer-I, the said Wash Buffer-I was prepared by making a solution containing 50 mM $Na_2HPO_4$, 0.3M NaCl, 1 mM AEBSF, 3M urea at pH7.4 with 0.1% Triton X-114 and 5-10 mM Imidazole. Next wash was performed in Wash Buffer-II, the said Wash buffer-II was prepared by making a solution containing the components 50 mM $Na_2HPO_4$, 0.3M NaCl, 1 mM AEBSF, 3-6M urea at pH7.4 with 0.1% Triton X-114 and 20 mM imidazole. Subsequently depending upon the initial concentration of urea used in example 2, further at least two or more washes were performed with Wash Buffer-III in presence of gradual decreasing urea concentrations, the said Wash Buffer-III was prepared by making a solution containing 50 mM $Na_2HPO_4$, 0.3 M NaCl, 1 mM AEBSF additionally with 20 mM imidazole with decreasing concentrations of urea. The said Wash buffer III did not contain TritonX-114 unlike Wash Buffer-II. The target protein of interest of the present invention was finally washed in the column using Wash Buffer III containing 50 mM $Na_2HPO_4$, 0.3M NaCl, 1 mM AEBSF under gradual decrease in concentration of urea and thereafter eluted from the column through an elution buffer 50 mM $Na_2HPO_4$, 0.3M NaCl, 1 mM AEBSF by increasing concentrations of imidazole (250-500 mM) with or without any urea at all.

Alternatively, during IMAC purification, washes are performed with Wash Buffer-III containing 50 mM $Na_2HPO_4$, 0.3M NaCl, 1 mM AEBSF in presence of 3-6M urea and subsequently the target protein of interest of the present invention is eluted from the column with an elution buffer comprising increasing concentration of imidazole (250-500 mM) in presence of 3-6M urea, 50 mM $Na_2HPO_4$, 1 mM AEBSF, 0.3 M NaCl.

Example 4: Dialysis of the Target Protein MEV1 and MEV2 and Size Exclusion Chromatography and Protein Refolding Ni-NTA column based affinity purified protein (MEV-1) was further dialyzed against PBS (phosphate buffered saline) in presence of refolding buffers comprising 0.1-0.3M NaCl, 10% glycerol and 0.2-0.5 M Arginine or 0.2-0.5 M Arginine-HCl using 10 kDa cut off dialysis bag to remove imidazole. Size exclusion chromatography was performed if necessary as final polishing step using sephacryl 200 or superdex 200 with automated chromatography system. Alternatively, urea denatured protein solution (of MEV-1) is either purified by IMAC purification and subsequently or directly refolded by dialysis using 10 kDa dialysis bag in presence of refolding buffers with gradual decreasing urea concentration and ending at zero or negligible urea concentration, 0.2-0.5 M Arginine or 0.2-0.5M Arginine-HCl, 10%-20% Glycerol. The refolded recombinant protein MEV1 is purified by size exclusion chromatography as single step purification or if required as final step of purification for IMAC purified protein using sephacryl 200 or sephadex 200 or superdex 200 with AKTA (automated chromatographic purifier, GE). On the other hand, MEV2 protein was refolded in decreasing urea (from 6M to 0.1 M) and DTT (from 20 mM to negligible concentrations or 0.1 mM or even less) concentration in presence of 0.2-1M Arginine or Arginine-HCL and/or redox pair reagents like Cysteine/Cystine or GSSG/GSH or oxidized DTT/reduced DTT or cystamine/cysteamine with concentrating between 0.05 mM to 10 mM. MEV2 protein is purified with size exclusion chromatography as mentioned above. Up to 96% pure protein of MEV2 can be achieved.

The protein was stored in polyols or sugars like 5-40% Glycerol or 5-60% sucrose or 5-40% Trehalose or 5-40% Sorbitol at −20° C. to (avoid repeated freeze thaw which can be detrimental for the protein) protect from thermal stress given in Table 4.

Example 5: Results and Outcome of IB Protein MEV1 Extraction and Purification The SDS-PAGE run of the eluted fractions from Ni-NTA columns (FIG. 5A) or direct purification by size exclusion chromatography showed the presence of up to ~94-96% respectively pure protein (Table 1 and 2). Western blot analysis with his tagged monoclonal antibody showed the specific expression of the desired recombinant protein in the blot (FIG. 5B).

TABLE 1

| Purity grade from IMAC and Size exclusion chromatography (Applicable for MEV1) | |
|---|---|
| Step | % age Purity |
| After Lysis | Between 22-28% |
| After Urea Denaturation | Between 50-60% |
| After IMAC purification | Between 90-94% purity |
| After Size exclusion chromatography | Between 92 upto 96% purity |

TABLE 2

| Purity Grade from Size exclusion chromatography Purification (Applicable for both MEV1 and MEV2) | |
|---|---|
| Step | % age Purity |
| After Lysis | Between 22-28% |
| After Urea Denaturation | Between 50 60% |
| After Size exclusion chromatography Purification | Upto 96% |

Example 6: Immunogenicity of MEV1 Recombinant Protein

All mice experiments were carried out strictly maintaining the procedure that will be approved by the Animal Experiment Committee. Groups of 6-week-old female BALB/c mice was inoculated with the recombinant protein alone, in combination with Freund's complete adjuvant (CFA) Sigma), alum, MPLA and Alum, Ribi adjuvant, PolyIC, AddaVax (MF59 like) or PBS.

All mice were then boosted twice with the same dose in Freund's incomplete adjuvant (IFA) or other respective adjuvants at a 2-week interval. Two-Three weeks after 1st immunization and/or two weeks after $2^{nd}$ and $3^{rd}$ immunization, serum samples were prepared and stored frozen until use. Animals were sacrificed after collecting the serum two weeks after the last immunization.

ELISA plates were coated with 0.5-1 μg of MEV1 antigen or synthetic peptides overnight in 0.1 M carbonate buffer (pH9.6). Next day, the plates were blocked for 1.5 hrs in 3% skimmed milk. Subsequently, serially diluted immunized sera were added in wells and incubated for 1.5 hrs. After several washes with phosphate buffered saline with Tween20 (PBST), the wells were incubated with 1:2000 diluted anti-mouse IgG HRP conjugated antibody (Thermo Scientific) or anti-mouse IgG1 HRP conjugated antibody (Thermo Scientific) or IgG2a HRP conjugated antibody (Abeam) and incubated for another 1 hr. After several washes with PBST and final wash with PBS, TMB (3, 3', 5, 5'-Tetraethylbenzidine) substrate for ELISA (Amresco) was added for color development and finally the reaction was stopped with 0.6-1M HCL.

Animal immunogenicity studies performed in presence of different adjuvants and subsequent analysis of the collected serum by ELISA has showed end-point titer ranging from 12500 to 100000 respectively in presence of different adjuvants (FIG. 8) ( ). IgG1/IgG2a ratio greater than 1 depicts immune response predominantly associated with Th2 lymphocytes and that of less than 1 denotes immune response predominantly associated with Th1 lymphocytes. The ratio of 12.04 was obtained after immunization with 10 μg of antigen and CFA adjuvant as prime dose and antigen with IFA adjuvant combination as $2^{nd}$ booster dose respectively (FIG. 6). The ratio was found to be 7.75 immunized with 10 μg of antigen with alum adjuvant as $2^{nd}$ booster dose (FIG. 6). The antibody elicited is specific and highly immunogenic in presence of alum and CFA/IFA adjuvants. The higher ratio of IgG1/IgG2a from the MEV1 immunized sera indicates the involvement of Th2 lymphocytes in the immune response Immunization in presence of IFA has elicited strong IgG1 response during terminal booster dose. MEV1 immunized sera in the presence of alum has been found to direct more IgG1 immune response indicating Th2 lymphocyte involvement that supports previous studies which have shown that alum is involved in Th2 associated immune response. On the contrary 10 μg of antigen formulated with MPLA+ Alum, Poly(I:C) or AddaVax generated slight higher IgG2a with IgG1:IgG2a ratio of 0.47, 0.76 and 0.44 indicating overall balanced Th1/Th2 immune response with slight biasness towards Th1 mediated immune response.

Inventors have also performed Interferon gamma (IFN-γ) and Interleukin-4 (IL-4) quantitative assay which represents Th1 and Th2 lymphocyte specific immune response respectively from splenocytes isolated from the mice immunized with MEV1 formulated with different adjuvants. Splenocytes were plated in the 24 well plate followed by stimulation with antigen or peptides. After 72 hrs, supernatant were collected and cytokine assays were performed using kits. We have found that recombinant antigen formulated with MPLA and Alum is inducing significant Interferon gamma while the formulation with alum is inducing comparatively more IL-4. Interferon gamma is the indicator for Th1 type response while IL4 is the indicator for Th2 type immune response. Thus, the formulation in presence of MPLA and alum is inducing more Th1 type immune response and that with only alum is inducing more Th2 specific immune response.

Immunofluorescence assay: Vero cells were infected with either EV71 or CVA16 virus at 0.1-0.2 MOI. One day post infection, the cells were fixed with methanol-acetone solution (1:1 v/v) for 1 hr. Then, the cells were blocked with 1-3% BSA for 1 hr. Subsequently, the cells were incubated with serially diluted serum for 1.5 hrs at room temperature or overnight at 4° C. After several washes with PBS, the cells were incubated with anti-mouse IgG Alexa Fluor 488 conjugated antibody (Thermo Scientific) for 1 hr and observed under fluorescence microscope.

Immunofluorescence assay with virus infected and mock infected Vero cell using serum raised against MEV1 as primary antibody showed that the antibody raised against MEV1 antigen binds with both EV71 and CVA16 viruses (FIG. 7). EV71 antigen specific titer of 6400 and CVA16 antigen specific titer of 800 is achieved with MEV1.

In vitro neutralization assay: In vitro neutralization was assessed by 50% reduction in Plaque (PRNT50). Vero cells were infected with pre-optimized countable Plaque forming units (PFU) of virus or mixture of virus and serially diluted sera (1:1) in 12 well format. After 1.5 hrs post infection, the cells were overlayered with 0.8% Carboxymethyl cellulose (CMC) (Sigma) in media. The cells were fixed in 10% formalin four days post infection and stained with 0.8% crystal violet solution for plaque visualization. PRNT50 was calculated as the highest sera dilution showing 50% or more reduction in the number of plaques.

It was found that MEV1 adjuvanted with MPLA and alum combination is showing highest neutralization titer against EV71 and CVA16 (Table 3).

TABLE 3

| PRNT50 titer | | |
|---|---|---|
| Adjuvant Formulation | EV71 | CVA16 |
| CFA/IFA | 40 | 20 |
| Alum | 30 | 15 |
| Alum + MPLA | 80 | 20 |
| Adavax (MF59 like) | 30 | 15 |
| Poly(I:C) | 30 | 15 |

The results obtained from immunofluorescence and $PRNT_{50}$ assay indicated the cross reactivity and cross-protectivity of the elicited antibody against both the viruses. Whole IgG, IgG isotype assay and cytokine assays showed that MEV1 can generate both cellular and humoral immune response significantly in present of appropriate adjuvants.

TABLE 4

| Stability studies with purified synthetic MEV-1 | | |
|---|---|---|
| | Temp | |
| Time | 4° C. (5 ± 3° C.) | 37 ± 2° C. |
| 1 week | 95% | >90% |
| 2 week | 95% | >70% |
| 1 month | 95% | |
| 3 month | 93% | |
| 6 month | 91% | |

I claim:

1. An immunogenic composition for inducing an immune response against Hand Foot and Mouth Disease caused by EV71 and CA16 comprising:

a. an antigen that is a synthetic construct selected from the recombinant protein sequences as represented by SEQ ID No. 2 (named as MEV1) and SEQ ID No. 4 (named as MEV2);

b. one or more adjuvants;

c. one or more stabilizers; and d. a physiologically acceptable buffer selected from phosphate or citrate buffer;

wherein the immunogenic composition is stable for at least 2 years at 5±3° C. and up to 2 weeks at 37° C.

2. The immunogenic composition of claim 1, wherein SEQ ID No. 2 is obtained from a codon optimized gene sequence as represented by SEQ ID No. 1.

3. The immunogenic composition claim 1, wherein SEQ ID No. 4 is obtained from a codon optimized gene sequence as represented by SEQ ID No. 3.

4. The immunogenic composition claim 1, wherein the adjuvant is alum, a squalene based adjuvants, montanide, a RIBI adjuvant, complete Freud's adjuvant, incomplete Freud's adjuvant, MPL, muramyl dipeptide, an oil-in-water emulsion, a TLR ligand based adjuvant, a CpG oligonucleotides, a Non-CpG oligonucleotide, a saponins, a vitamin, or an immunomodulant.

5. The immunogenic composition of claim 1, wherein the stabilizer is a sugar or a sugar alcohol.

6. The immunogenic composition of claim 1, wherein antigens SEQ ID No. 2 and SEQ ID No. 4 are prepared by a process comprising:

a. expression of the protein sequences SEQ ID No. 2 and SEQ ID No. 4 from codon optimized gene sequences with 0.2-0.75 mM IPTG between 15° C.-37° C., in the form of inclusion bodies in a suitable host that is *E. coli* BL21 (DE3) cells or Rosetta cells;

b. centrifugation at 10,000 rpm for 5 minutes to obtain the protein of interest in the cell pellet;

c. suspending the pellet of step (b) with lysis buffer-I for MEV1 that comprises 50 mM $Na_2HPO_4$, 0.3M NaCl, 1% TritonX-114, 0.5 mg/ml lysozyme, and 1 mM AEBSF, simultaneously performing freeze thaw cycles for at least 3 times followed by ultrasonication for 20 seconds, with at least 30 seconds intervals in between;

d. alternatively undergoing lysis with lysis buffer-I for MEV2 that comprises 50 mM Tris, 0.3 M NaCl, 1% Triton X114, 0.5 mg/ml lysozyme, and 1 mM AEBSF at pH 8-8.5;

e. undergoing cell lysis with lysis buffer-II for MEV1 that comprises 3-6M Urea, 5-10 mM imidazole, 50 mM $Na_2HPO_4$, 0.3M NaCl, and 1 mM AEBSF at 4° C. for 3-16 hours to recover the insoluble protein at pH of 7.4 for MEV1 to obtain a denatured protein solution of MEV1;

f. alternatively undergoing cell lysis with lysis buffer-II for MEV2 that comprises 50 mM Tris, 0.3 M NaCl, and 1 mM AEBSF in presence of 6M urea and 10-20 mM DTT;

g. adding the denatured protein solution of step (e) to Ni-NTA Immobilized Metal Affinity Chromatography column followed by washing with wash buffer-I comprising 50 mM $Na_2HPO_4$, 0.3M NaCl, 1 mM AEBSF, and 3M urea at pH7.4 with 0.1% Triton X-114 and 5-10 mM Imidazole;

h. again performing washing after step (g) for MEV1 with Wash Buffer-II that comprises 50 mM $Na_2HPO_4$, 0.3M NaCl, 1 mM AEBSF, and 3-6M urea at pH7.4 with 0.1% Triton X-114 and 20 mM imidazole; followed by washing by Wash Buffer-III that comprises 50 mM $Na_2HPO_4$, 0.3 M NaCl, and 1 mM AEBSF additionally with 20 mM imidazole with decreasing concentrations of urea;

i. eluting the target protein MEV1 with elution buffer that comprises 50 mM $Na_2HPO_4$, 0.3M NaCl, 1 mM AEBSF by increasing concentrations of imidazole optionally with 3-6 M urea;

j. undergoing dialysis of MEV-1 after step (i) against phosphate buffer saline using 10 kDa cutoff, membrane and refolding with refolding buffers comprising 0.1-0.3M NaCl, 10% glycerol and 0.2-0.5 M Arginine or 0.2-0.5 M Arginine-HCl optionally followed by size exclusion chromatography to obtain the final protein MEV-1 with 92% to 96% purity;

k. undergoing refolding of MEV-2 after step (f) in decreasing urea and DTT concentration in presence of 0.2-1M Arginine or Arginine-HCL, a redox pair reagent that is Cysteine/Cystine, GSSG/GSH, oxidized DTT/reduced DTT or cystamine/cysteamine with concentration between 0.05 mM to 10 mM to obtain the final protein MEV-2 with at least 96% purity.

7. A method of preparing the immunogenic composition of claim 1, comprising the steps:

a. expression of the protein sequences SEQ ID No. 2 and SEQ ID No. 4 from codon optimized gene sequences with 0.2-0.75 mM IPTG between 15° C.-37° C., in the form of inclusion bodies in a suitable host selected from *E. coli* BL21 (DE3) cells or Rosetta cells;

b. centrifugation at 10,000 rpm for 5 minutes to obtain the protein of interest in the cell pellet;

c. suspending the pellet of step (b) with lysis buffer-I that comprises 50 mM $Na_2HPO_4$, 0.3M NaCl, 1% TritonX-114, 0.5 mg/ml lysozyme, and 1 mM AEBSF, simultaneously performing freeze thaw cycles for at least 3 times followed by ultrasonication for 20 seconds with at least 30 seconds intervals in between;

d. alternatively undergoing lysis with lysis buffer-I for MEV2 that comprises 50 mM Tris, 0.3 M NaCl, 1% Triton X114, 0.5 mg/ml lysozyme, 1 mM AEBSF at pH 8-8.5;

e. undergoing cell lysis with lysis buffer-II for MEV1 that comprises 3-6M Urea, 5-10 mM imidazole, 50 mM $Na_2HPO_4$, 0.3M NaCl, and 1 mM AEBSF at 4° C. for 3-16 hours to recover the insoluble protein at pH of 7.4 for MEV1 to obtain a denatured protein solution of MEV1;

f. alternatively undergoing cell lysis with lysis buffer-II for MEV2 that comprises, 50 mM Tris, 0.3 M NaCl, and 1 mM AEBSF in presence of 6M urea and 10-20 mM DTT;

g. adding the denatured protein solution of step (e) to Ni-NTA Immobilized Metal Affinity Chromatography column followed by washing with wash buffer-I that comprises 50 mM $Na_2HPO_4$, 0.3M NaCl, 1 mM AEBSF, and 3M urea at pH7.4 with 0.1% Triton X-114 and 5-10 mM Imidazole;

h. again performing washing after step (g) for MEV1 with Wash Buffer-II that comprises 50 mM $Na_2HPO_4$, 0.3M NaCl, 1 mM AEBSF, and 3-6M urea at pH7.4 with 0.1% Triton X-114 and 20 mM imidazole; followed by washing by Wash Buffer-III that comprises 50 mM $Na_2HPO_4$, 0.3 M NaCl, and 1 mM AEBSF additionally with 20 mM imidazole with decreasing concentrations of urea;

i. eluting the target protein MEV1 with elution buffer that comprises 50 mM $Na_2HPO_4$, 0.3M NaCl, and 1 mM AEBSF by increasing concentrations of imidazole optionally with 3-6 M urea;

j. undergoing dialysis of MEV-1 after step (i) against phosphate buffer saline using 10 kDa cutoff, membrane and refolding with refolding buffers comprising 0.1-0.3M NaCl, 10% glycerol and 0.2-0.5 M Arginine or 0.2-0.5 M Arginine-HCl optionally followed by size exclusion chromatography to obtain the final protein MEV-1 with 92% to 96% purity;

k. undergoing refolding of MEV-2 after step (f) in decreasing urea and DTT concentration in presence of 0.2-1M Arginine or Arginine-HCL, redox pair reagents that is Cysteine/Cystine, GSSG/GSH, oxidized DTT/reduced DTT or cystamine/cysteamine with concentration between 0.05 mM to 10 mM to obtain the final protein MEV-2 with at least 96% purity.

8. A composition comprising a multi-epitope synthetic protein sequence as disclosed in SEQ ID No. 2, the composition having at least 92%-96% purity.

9. A composition comprising a multi-epitope synthetic protein sequence as disclosed in SEQ ID No. 4, the composition having with at least 96% purity.

10. The immunogenic composition of claim 4, wherein the alum is aluminum phosphate or aluminum hydroxide.

11. The immunogenic composition of claim 4, wherein the saponin is QS-1, ISCOM, or ISCOMATRIX.

12. The immunogenic composition of claim 4, wherein the immunomodulant is a cytokine.

13. The immunogenic composition of claim 4, wherein the squalene based adjuvant is MF59.

14. The immunogenic composition of claim 5, wherein the sugar is 5-60% sucrose or 5-40% trehalose.

15. The immunogenic composition of claim 5, wherein the sugar alcohol is 5-40% glycerol or 5-40% sorbitol.

16. The immunogenic composition of claim 6, wherein the codon optimized sequences are SEQ ID No. 1 and SEQ ID No. 3, respectively.

17. The immunogenic composition of claim 7, wherein the codon optimized sequences are SEQ ID No. 1 and SEQ ID No. 3, respectively.

* * * * *